(12) United States Patent
Dominick et al.

(10) Patent No.: US 9,619,496 B2
(45) Date of Patent: Apr. 11, 2017

(54) METHOD, COMPUTER READABLE MEDIUM AND SYSTEM FOR USING LARGE DATA SETS IN VIRTUAL APPLICATIONS

(75) Inventors: Lutz Dominick, Eggolsheim (DE); Chiheb Charrad, Neunkirchen Am Brand (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1161 days.

(21) Appl. No.: 13/328,246

(22) Filed: Dec. 16, 2011

(65) Prior Publication Data
US 2013/0160000 A1 Jun. 20, 2013

(51) Int. Cl.
G06F 9/455 (2006.01)
G06F 17/30 (2006.01)
G06F 9/445 (2006.01)
G06F 19/00 (2011.01)

(52) U.S. Cl.
CPC ........ *G06F 17/30312* (2013.01); *G06F 9/445* (2013.01); *G06F 19/30* (2013.01); *G06F 19/32* (2013.01); *G06F 19/321* (2013.01); *G06F 19/322* (2013.01)

(58) Field of Classification Search
CPC .. G06F 17/30312; G06F 19/32; G06F 3/1415; G06F 9/445; G06F 19/322; G06F 19/321
USPC .................................. 707/622; 718/1; 726/1
See application file for complete search history.

(56) References Cited

U.S. PATENT DOCUMENTS

| | | | | |
|---|---|---|---|---|
| 6,327,594 B1* | 12/2001 | Van Huben | ....... | G06F 17/30348 |
| 6,401,138 B1* | 6/2002 | Judge | .................... | G06F 9/4443 |
| | | | | 705/2 |
| 6,608,628 B1* | 8/2003 | Ross | ....................... | G06T 17/20 |
| | | | | 345/619 |
| 7,346,648 B1* | 3/2008 | Seliger | ................. | G06F 19/322 |
| | | | | 705/2 |
| 8,254,704 B2* | 8/2012 | Lu | ......................... | G06F 3/1415 |
| | | | | 382/224 |
| 8,387,048 B1* | 2/2013 | Grechishkin et al. | ............ | 718/1 |
| 8,392,902 B2* | 3/2013 | Reinz | ....................... | G06F 8/67 |
| | | | | 250/363.02 |
| 8,893,120 B2* | 11/2014 | Pinsky | ......................... | 717/174 |
| 8,924,881 B2* | 12/2014 | Martin | ................ | G06F 19/322 |
| | | | | 715/772 |
| 2003/0158753 A1* | 8/2003 | Bernston et al. | ................. | 705/2 |
| 2003/0200116 A1* | 10/2003 | Forrester | ............... | G06F 19/321 |
| | | | | 705/2 |
| 2006/0053195 A1* | 3/2006 | Schneider | .......... | H04L 12/1827 |
| | | | | 709/204 |

(Continued)

*Primary Examiner* — Lewis A Bullock, Jr.
*Assistant Examiner* — Gilles Kepnang
(74) *Attorney, Agent, or Firm* — Harness, Dickey & Pierce

(57) ABSTRACT

A method, computer readable medium and system are disclosed. The system includes one or more first interfaces communicatively coupled to a data storage device and one or more second interfaces communicatively coupled to a user interface, the control module being configured to share data, retrieved from the data storage device, across a plurality of virtual applications. The system further includes an application controller communicatively coupled to the control module, the application controller being configured to select at least one of the virtual applications based on information received via the at least one of the one or more second interfaces.

20 Claims, 6 Drawing Sheets

(56) References Cited

U.S. PATENT DOCUMENTS

| | | | |
|---|---|---|---|
| 2006/0252998 A1* | 11/2006 | Kimbrell | H04M 1/72536 600/300 |
| 2007/0192354 A1* | 8/2007 | Wei et al. | 707/102 |
| 2007/0256073 A1* | 11/2007 | Troung | G06F 21/606 718/1 |
| 2008/0098046 A1* | 4/2008 | Alpern et al. | 707/203 |
| 2009/0077157 A1* | 3/2009 | Ma et al. | 709/201 |
| 2009/0113413 A1* | 4/2009 | Reinz | G06F 19/3412 717/173 |
| 2009/0217340 A1* | 8/2009 | Sitomer et al. | 726/1 |
| 2009/0288064 A1* | 11/2009 | Yen et al. | 717/106 |
| 2009/0307705 A1* | 12/2009 | Bogner | G06F 9/5077 718/104 |
| 2010/0169642 A1* | 7/2010 | Wise | G06F 19/321 713/164 |
| 2010/0228699 A1* | 9/2010 | Webber et al. | 707/622 |
| 2010/0317953 A1* | 12/2010 | Reggiardo | G06F 19/3412 600/365 |
| 2011/0126143 A1* | 5/2011 | Williams | G06F 3/0488 715/771 |
| 2011/0191767 A1* | 8/2011 | Pinsky | G06F 9/445 717/176 |
| 2011/0246565 A1* | 10/2011 | Irwin | G06F 19/322 709/203 |
| 2011/0321175 A1* | 12/2011 | Slater | G06F 21/552 726/28 |
| 2013/0311926 A1* | 11/2013 | Keegan | G06F 19/3418 715/771 |

* cited by examiner

CONVENTIONAL ART

METHOD, COMPUTER READABLE MEDIUM AND SYSTEM FOR USING LARGE DATA SETS IN VIRTUAL APPLICATIONS

BACKGROUND

Field

Embodiments generally relate to providing access to large data sets in systems using virtual applications.

Related Art

Large medical applications manage large amounts of data and consume considerable resources (e.g., processing and memory resources). For example, the diagnosis of a heart that analyzes the ventricle and the vessels in 2D and 3D, based on one large data set of the heart (e.g., a computed tomography scan).

The large size of the medical application enlarges start-up times and also the time a user needs to switch between applications in order to perform application specific objectives needed for a diagnosis. The large amount of data causes considerable load times and the necessary memory consumption can be large enough to block other users on a server hosting the data. Limitations associated with a display device and constraints associated with usability (e.g., legal and technical) do not always allow for including all functionality into one giant diagnosis application.

As a result, the known approaches include tying clinical diagnosis workflows to a series of specialized applications. This may minimize the size of the application and the limitations associated with a display device. Each specialized application allows the user to alter the medical data accordingly. On the other hand, these specialized applications alter the large amount of data independently of each other.

As a result, the data is reproduced across each of the specialized applications, in addition to cross application notification and integration complexities, in order to consolidate the result set in the end and allow a hand-over to the next workflow step. Further if the specialized applications reload intermediate results in order to allow continue working, the re-distribution of the data creates additional complexity and footprint growth.

Without additional complex systems, the stepwise diagnosis requires seeing changes in all contributing applications. A selected application has to reload the changed data again and merge the selected application's changes to the data at the same time, which gives contradictions, which increases the load time of the selected application and because the selected application code base has to behave like the foreign application in order to show the user a consolidated change state of the data (also across applications) and even allow editing, thus again behave like a large application.

FIG. 1 illustrates conventional art client-server system. As shown in FIG. 1, the client-server system 100 includes a client (or front end) 105 and a server (or back end) 110. The client 105 includes a processor 120, a memory 125, an operating system 140 and a virtual application (VAP) 150. The server 110 includes a processor 130, a memory 135, an operating system 145, a virtual application (VAP) 155 and data 160.

A virtual application may describe software technologies that improve portability, manageability and compatibility of applications by encapsulating them from the underlying operating system on which they are executed, and from the product specific run-time infrastructure that hosts and services applications. A virtual application may be software executing on a physical machine which emulates an independent and separate application from other virtual applications which may be emulated on a physical machine (e.g., a client, a server or a physical entity).

A single physical machine may host multiple virtual applications. A virtual application may emulate physical machine and be known in the art as a virtual machine. A virtual application may emulate a known software application. For example, the virtual application may emulate a word processor, imaging editing software, software to operate a device (e.g., a medical imaging device) and the like. For virtual machines, the same holds as for physical machines.

As is shown in FIG. 1 VAP 150 and VAP 155 may interact with each other. For example, in a client-server system a client virtual application (e.g., VAP 150) may perform a user interface function. For example, the client virtual application may display images or data, provide user input/output, control peripheral devices and the like. In a client-server system, a server virtual application (e.g., VAP 155) may perform a back end function. For example, the server virtual application may provide access to data (e.g., data 160) to the client virtual application.

In a standalone system (e.g., no client-server relationship) one virtual application (e.g., VAP 150) may perform both the client and the server functions. For example, the one virtual application may provide both a user interface function and a data access function.

As is known, one client may be configured to run a plurality of virtual applications. The plurality of virtual applications may be standalone or interact with a server. If each of the plurality of virtual applications access a same data set (e.g., medical image data), the same data set is replicated for each of the plurality of virtual applications. This data replication results in over utilization of system resources (e.g., processor and memory resources).

As one skilled in the art will appreciate, as the size of the data set increases and/or the number of virtual applications increases, system resources will be strained. As a result, system designers over scale the quantity of resources resulting in excess costs in the manufacture of devices (e.g., medical imaging devices), or generate complex and costly resource management, with potentially limited success. Alternatively, system designers allow for reduced system performance as system resources are strained, or alternatively, let the user adjust to poor system performance.

SUMMARY

The inventors have recognized, in the context of a system utilizing large data sets (e.g., medical image data), a new system to provide access to a data set such that each of a plurality of virtual applications utilize one instance of the data set. At the same time, these virtual applications remain as independent as if they were stand-alone physical applications, for example, during editing an instance of the data set.

One embodiment of the present application includes an apparatus (e.g., a standalone computer, a client and/or a server includes a control module). The apparatus includes one or more first interfaces communicatively coupled to a data storage device and one or more second interfaces communicatively coupled to a user interface, the control module being configured to share data, retrieved from the data storage device, across a plurality of virtual applications. The standalone computer, a client and/or a server further includes an application controller communicatively coupled to the control module, the application controller being configured to select at least one of the virtual applications based on information received via the at least one of the one or more second interfaces.

One embodiment of the present application includes a method. The method includes associating a plurality of virtual applications with a shared data and associating a controller with the plurality of virtual applications such that the controller enables a first one or more virtual applications of the plurality of virtual applications to use the shared data and the controller excludes a second one or more virtual applications of the plurality of virtual applications from using the shared data.

One embodiment of the present application includes a computer readable medium. The computer readable medium includes code segments that, when executed by a processor, cause the processor to associate a plurality of virtual applications with a shared data and associate a controller with the plurality of virtual applications such that the controller enables a first one or more virtual applications of the plurality of virtual applications to use the shared data and the controller excludes a second one or more virtual applications of the plurality of virtual applications from using the shared data.

BRIEF DESCRIPTION OF THE DRAWINGS

The present invention will become more fully understood from the detailed description of example embodiments given herein below and the accompanying drawings, wherein like elements are represented by like reference numerals, which are given by way of illustration only and thus are not limiting of the present invention and wherein.

Figure 1:
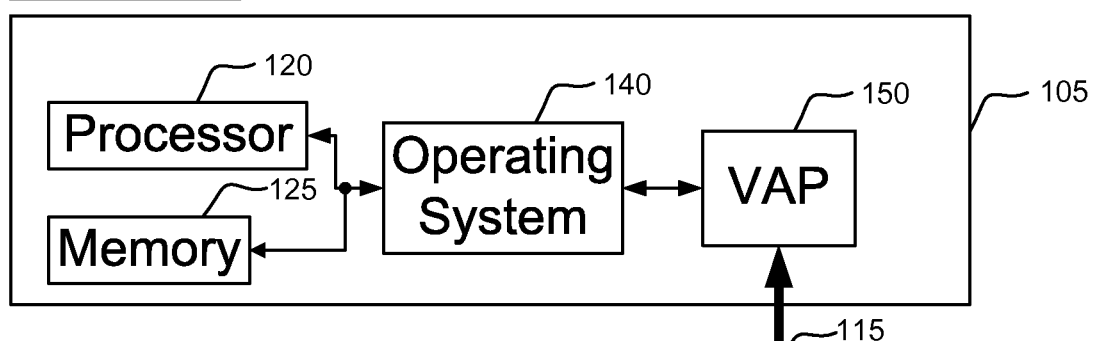
FIG. 1 illustrates a conventional art client-server system.
Figure 1:
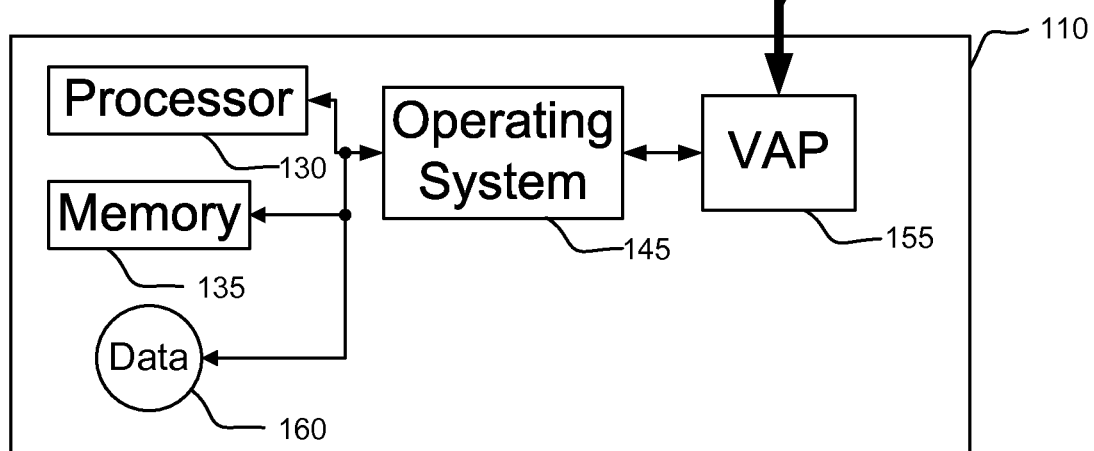

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EMBODIMENTS

While example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments will be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

An example embodiment includes a configurable, run-time adaptable and distributed physical architecture for virtual applications. According to the example embodiment, a layered architecture may be duplicated vertically and horizontally.

According to an example embodiment a standalone computer, a client and/or a server includes a control module including one or more first interfaces communicatively coupled to a data storage device and one or more second interfaces communicatively coupled to a user interface, the control module being configured to share data, retrieved from the data storage device, across a plurality of virtual applications. The standalone computer, a client and/or a server further includes an application controller communicatively coupled to the control module, the application controller being configured to select at least one of the virtual applications based on information received via the at least one of the one or more second interfaces.

Figure 2:
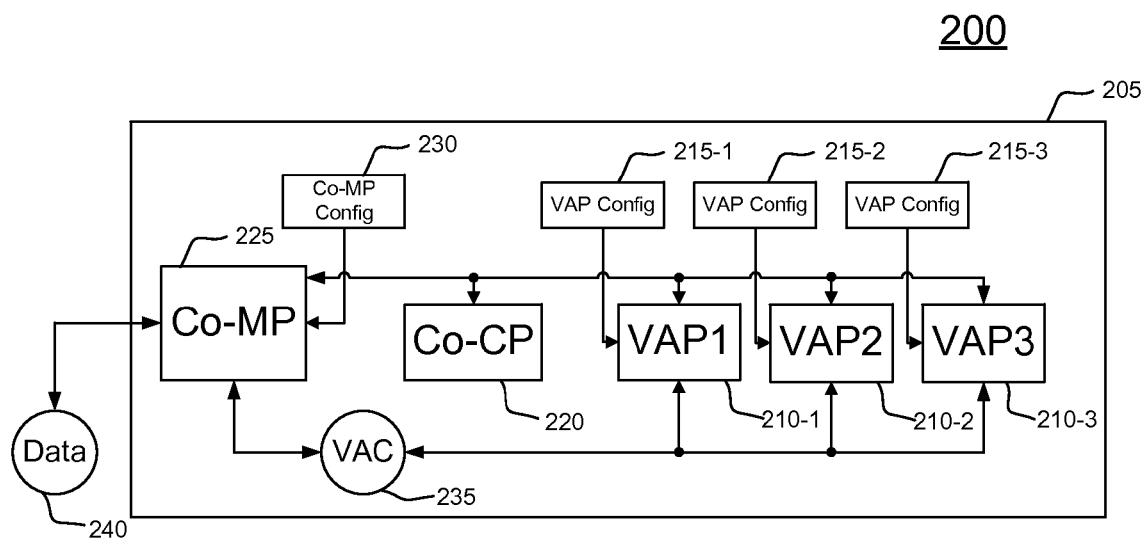
FIG. 2 illustrates a virtual application system according to at least one example embodiment.

FIG. 2 illustrates a virtual application system 205 according to an example embodiment. The virtual application system 205 may be associated with a client (e.g., client 105 as illustrated in FIG. 1) or a server (e.g., server 110 as illustrated in FIG. 1). Although not shown in FIG. 2, as one skilled in the art will appreciate, the virtual application system 205 according to an example embodiment may include a processor (e.g., processor 120 and/or 130), a memory (e.g., memory 125 and/or 130) and an operating system (e.g., operating system 140 and/or 145).

As shown in FIG. 2, the virtual application system 205 includes one or more virtual applications (VAP) 210-1, 210-2, 210-3 and one or more virtual application configuration files (VAP Config) 215-1, 215-2, 215-3. Although three virtual applications are shown, example embodiments are not limited thereto. The virtual application system 205 further includes a core content page (Co-CP) 220, a core master page (Co-MP) 225, a core master page configuration file (Co-MP Config) 230, a virtual application controller (VAC) 235 and data 240. The data 240 may be associated with, for example, data stored in and accessed via a database.

As shown in FIG. 2, the Virtual Application Controller (VAC) 235 is communicatively coupled to the core master page (Co-MP) 225 and each of the virtual applications (VAP) 210-1, 210-2, 210-3. The VAC 235 may control the structure of the core physical architecture during run-time. The VAC 235 creates a core structure of components and pages that loads data 240 that is associated with a plurality of virtual applications (e.g., VAP 210-1, 210-2 and 210-3). The VAC 235 presents a user (via a user interface described in more detail below) a list of applications (e.g., VAP 210-1, 210-2 and 210-3) the user can invoke in whatever order, each of these applications may work on (e.g., view or modify) the loaded data. As one skilled in the art will appreciate, the user is unaware of the nature of the application. In other words, the user is unaware that the applications being used are virtual applications.

As shown in FIG. 2, the core master page (Co-MP) 225 is communicatively coupled with the VAC 235 and data 240. The Co-MP 225 may master the configured set of VAPs and hosts ports for data (e.g., data 240) and event or trigger input and output (e.g., via a user interface described in more detail below). The Co-MP 225 preloads the data for the VAPs. The Co-MP 225 communicates (e.g., via a message) with the VAC 235 to launch a randomly chosen VAP (e.g., VAP 210-1) upon request of the user.

The core master page (Co-MP) 225 may associate the data 240 with selected virtual applications and disassociate other (non-selected) virtual applications from the data 240. Associating the data 240 may include enabling the selected virtual applications to modify the data 240.

The core configuration (Co-MP Config) 230 may include configure information associated with the intended set of virtual applications (e.g., VAP 210-1, 210-2 and 210-3) the user may access and launch. The core configuration 230 may be a file of a known standard (e.g., XML). The core configuration 230 may include dedicated files in a directory tree. For example, the core configuration 230 may include an application name, a position in the control area on the user interface, a link to the VAP configuration file (e.g., VAP Config 215-1, 215-2, 215-3), which is processed when a selected application is started. The Core Configuration 230 may also instruct a run-time engine associated with the user interface (described in more detail below) to start only the Co-MP 225.

In addition to the description above, the virtual applications (e.g., VAP 210-1, 210-2 and 210-3) may configure information associated with pluggable extension codes and their associated configuration VAP configuration (e.g., VAP Config 215-1, 215-2, 215-3) to allow representation on the user interface with, for example, known specialized display protocols and editing tools.

The core content page (Co-CP) 220 may host application content, associated with a specific VAP, and may decouple the actual virtual applications (e.g., VAP 210-1, 210-2 and 210-3) from the physical architecture. For example, the core content page (Co-CP) 220 may be a hosting module communicatively coupled to each of the plurality of virtual applications and configured to de-couple the virtual applications from a processor and/or an operating system. As is known, in a virtual application environment the physical architecture is typically transparent to the user. The core content page 220 may be the first component for every virtual application started by the user, and the core content page 220 may be active so long as the Co-MP 225 is active.

The core content page 220 may host, for example, mechanisms for editing, merge-back and availability of editing results. Mechanisms for editing, merge-back and availability of editing results are known to those skilled in the art and will not be described further for the sake of brevity. Further, if the user switches between virtual applications (e.g., VAP 210-1, 210-2 and 210-3) without closing them, the Co-CP 220 may reuse instances of virtual applications over and over to restore a former state for the user.

Referring to FIG. 2, for example, a user may launch a user interface including a plurality of applications. The applications may be virtual applications (e.g., VAP 210-1, 210-2 and 210-3). The launching of the user interface may activate Co-MP 225 and may associate the Co-MP 225 with the user interface. Further, VAC 235 and Co-CP 220 may be activated and associated with the Co-MP 225 as well. The Co-MP 225 may master VAP 210-1, 210-2 and 210-3 and may host ports for data 240. Alternatively, for one Co-MP 225 multiple Co-CP 220 may be activated based on the run-time exploration of the configurations in the multiple VAP-Config 215-1, 215-2 and 215-3 files, for example, if VAP 210-1 requires extended display rendering capabilities that may be incompatible to VAP 210-2 display rendering, while both VAP 210-1 and VAP 210-2 work on the data 240.

In the known virtual application architectures, data 240 would be instantiated and loaded into local memory three times (one for each of VAP 210-1, 210-2 and 210-3). However, according to an example embodiment of the present application, one instance of data 240 is associated with all three of VAP 210-1, 210-2 and 210-3. As the user switches between each of VAP 210-1, 210-2 and 210-3, the VAC 235 associates data 240 with the selected virtual application. Further, all applications can show an evolving edit state that is consolidated and consistent. In other words, if one of the virtual applications (e.g., VAP 210-1) edits the data 240, that change in data is almost instantly available to each of the other virtual applications (e.g., 210-2 and 210-3). Applications (e.g., VAP 210-1, 210-2 and 210-3) may be installed, updated, and released independently of each other.

One skilled in the art will appreciate that the 'virtuality' of an application is that the application shares a data 240 and a CO-MP 225 instance with one or more applications. In addition, the application may share a CO-CP 220 instance. Because the shared elements (e.g., Co-MP 225 and Co-CP 220) may not be associated with a standalone application. The elements (e.g., Co-MP 225 and Co-CP 220) may be associated the virtual application mechanism as a whole.

As one skilled in the art will appreciate, if VAC 235 is not used, none of the applications are virtual any more, and the formerly shared elements (e.g., data 240 and a CO-MP 225) may be instantiated once per application, turning each application to a standalone application, not a virtual application.

Figure 3:
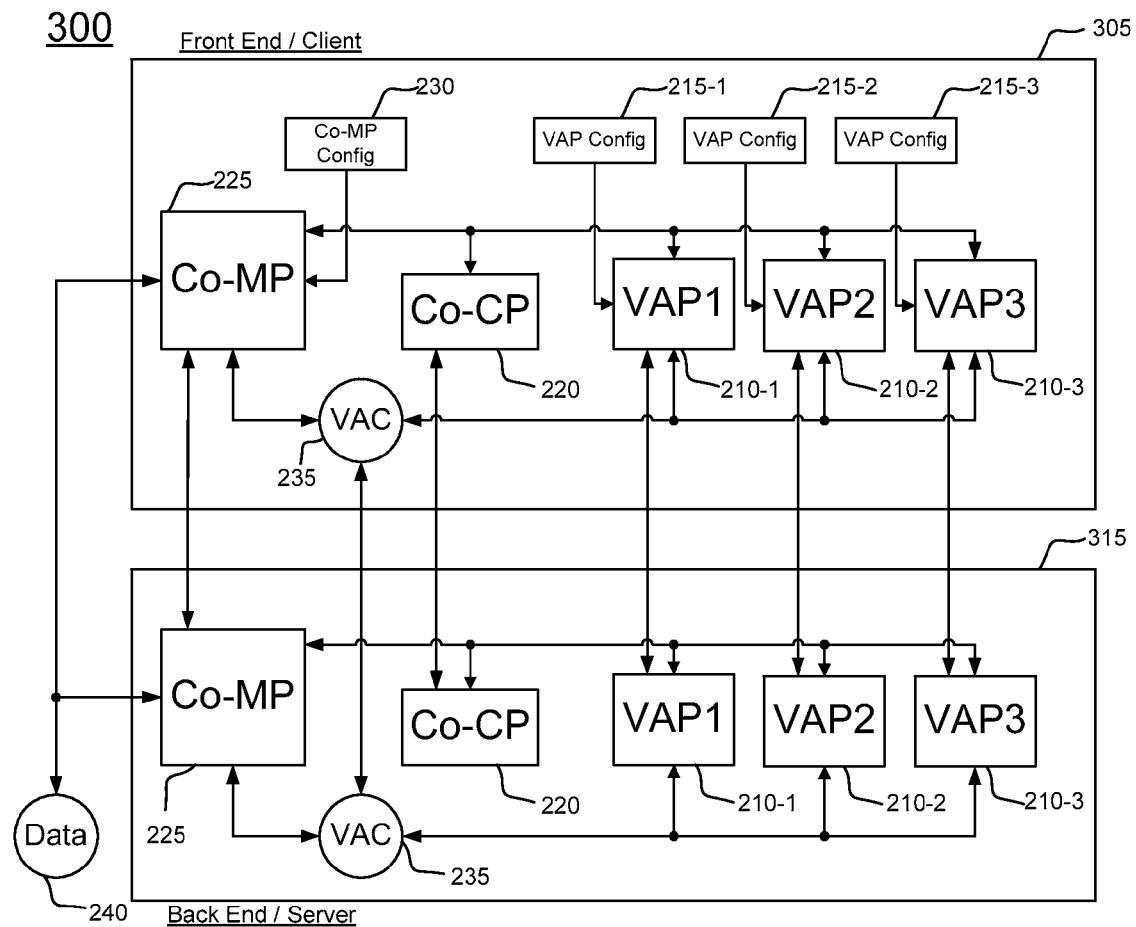
FIG. 3 illustrates a client-server system according to at least one example embodiment.

FIG. 3 illustrates a client-server system 300 according to an example embodiment of the present application. As shown in FIG. 3, the client-server system 300 includes a client (or front end) 305 and a server (or back end) 310. As one skilled in the art will recognize, the client 305 and the server 310 include elements (or a subset thereof) of the virtual application system 205. Further, although not shown in FIG. 3, as one skilled in the art will appreciate, the client-server system 300 according to an example embodiment may include a processor (e.g., processor 120 and/or 130), a memory (e.g., memory 125 and/or 130) and an operating system (e.g., operating system 140 and/or 145). In other words, the client-server system 300 may implement the virtual application system 205 (as illustrated in FIG. 2) into the client-server system 100 (as illustrated in FIG. 1). Like elements will not be discussed further for the sake of brevity.

As shown in FIG. 3, each of the like elements (e.g., Co-MP 225) of the client 305 and the server 310 are communicatively coupled with each other. For example, the Co-MP 225 associated with the client 305 is communicatively coupled with the Co-MP 225 associated with the server 310; the Co-CP 220 associated with the client 305 is communicatively coupled with the Co-CP 220 associated with the server 310; the VAC 235 associated with the client 305 is communicatively coupled with the VAC 235 associated with the server 310; and each of the virtual applications (e.g., VAP 210-1, 210-2 and 210-3) associated with the client 305 are communicatively coupled with the corresponding virtual applications (e.g., VAP 210-1, 210-2 and 210-3) associated with the server 310.

Referring to FIG. 3, for example, a user may launch a user interface including a plurality of applications. The applications may be virtual applications (e.g., VAP 210-1, 210-2 and 210-3). The launching of the user interface may activate Co-MP 225 and may associate the Co-MP 225 (in both the client 305 and the server 310) with the user interface. Further, VAC 235 and Co-CP 220 (in both the client 305 and the server 310) may be activated and associated with the corresponding Co-MP 225 as well. The Co-MP 225 may master VAP 210-1, 210-2 and 210-3. Further, preferably Co-MP 225 in the server 310 may host ports for data 240. Alternatively, Co-MP 225 in the client 305 may host ports for data 240.

Figure 4:
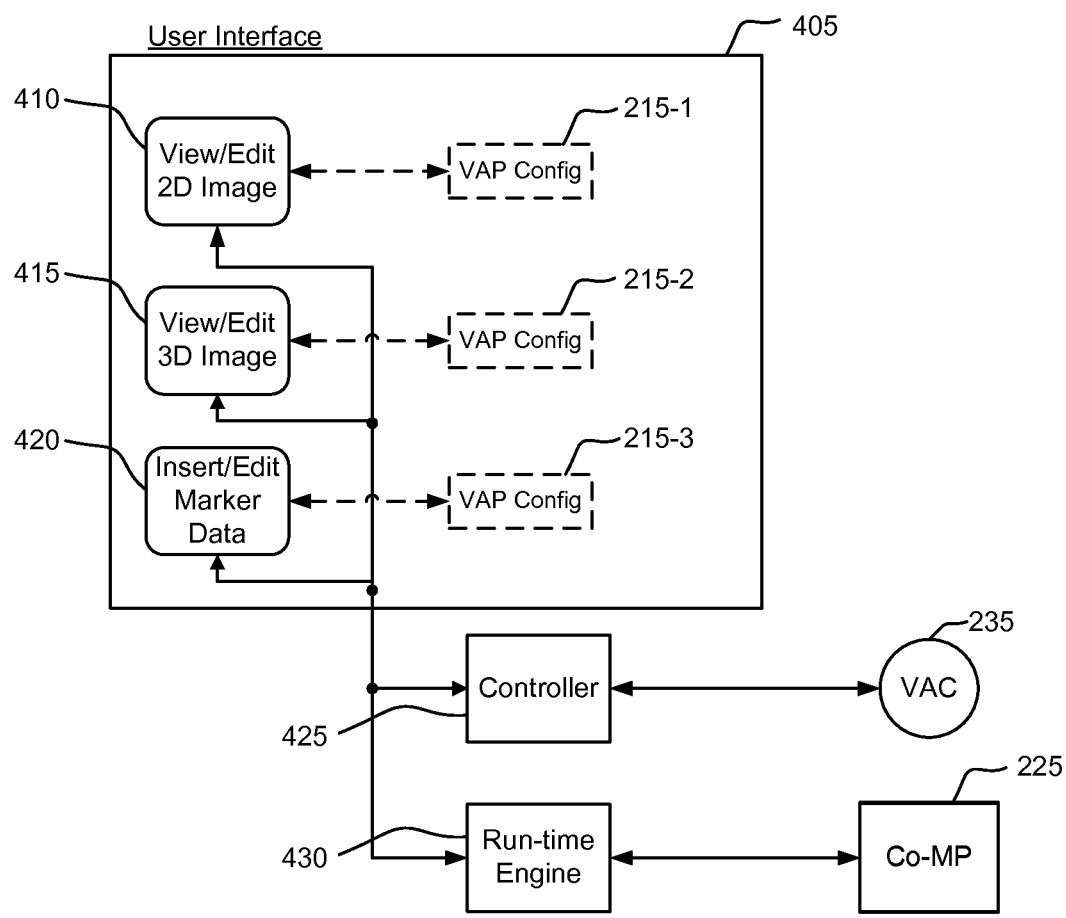
FIG. 4 illustrates a user interface system according to at least one example embodiment.

FIG. 4 illustrates a user interface system 400 according to an example embodiment of the present application. As shown in FIG. 4, the user interface system 400 includes a user interface 405, a first application module 410, a second application module 415 and a third application module 420. Although three application modules are shown, example embodiments are not limited thereto. Further, as an example, each of the application modules are shown with an exemplary function (e.g., View/Edit 2D image), however, example embodiments are not limited thereto.

As shown in FIG. 4, each of the application modules 410, 415, 420 are associated with a corresponding VAP Config 215-1, 215-2, 215-3 described in more detail above with regard to FIG. 2. The application modules 410, 415, 420 provide the control mechanisms for using virtual applications (e.g., VAP 210-1). For example, the control mechanisms may be editing, viewing, displaying information and the like.

The user interface system 400 further includes a controller 425 and a run-time engine 430. The controller 425 is communicatively coupled with each of the application modules 410, 415, 420, the run-time engine 430 and the VAC 235 (described in more detail above with regard to FIG. 2). The run-time engine 430 is communicatively coupled with each of the application modules 410, 415, 420, the controller 425 and the Co-MP 225 (described in more detail above with regard to FIG. 2).

Each of the application modules 410, 415, 420 may provide the user functionality and control mechanisms associated with a virtual application (e.g., VAP 210-1). For example, each of the application modules 410, 415, 420 may display information (e.g., image data), provide the mechanism for data entry (e.g., insert markers on image data), provide the mechanism for editing data (e.g., crop image data), and the like.

The controller 425 may read a user input from one or more of the application modules 410, 415, 420, interpret the input as, for example an instruction and forward the instruction to the VAC 235. For example, if the user switches from application module 410 (View/Edit 2D Image) to application module 415 (View/Edit 3D Image), the controller reads and interprets the switch and communicates an instruction to the VAC 235. The VAC 235 will then de-activate VAP 210-1 (associated with View/Edit 2D Image through VAP Config 215-1) and activate VAP 210-2 (associated with View/Edit 3D Image through VAP Config 215-2).

The run-time engine 430 may be instantiated when a user opens an interface (e.g., user interface 405). Upon instantiation, the run-time engine 430 starts the Co-MP 225 associated with the user interface 405. As described above, the Co-MP 225 masters the configured set of VAPs and hosts ports for data (e.g., data 240) and event or trigger input and output. For example, associates all of the virtual applications (e.g., VAP 210-1, 210-2 and 210-3) with the user interface 405.

At run-time, the physical architecture (e.g., client 305 and/or server 310) may be controlled by the Virtual Application Controller (VAC) 235, which creates a core structure of components and pages that loads the data to work on and presents the user a list of applications he can invoke in whatever order, all of these applications can work on the loaded data. On demand, the user launches his selected application with the right data, which may load with minimal delay, and the user may switch from one application to any other application instantly and without a flickering user interface. In effect, all data may be loaded once and edited by one application at a time, while all applications may show an evolving edit state that is consolidated and consistent. All applications may be installed, updated, and released independently of each other.

According to an example embodiment of the present application, a method includes associating a plurality of virtual applications with a shared data and associating a controller with the plurality of virtual applications such that the controller enables at least a first of the plurality of virtual applications to use the shared data and the controller excludes at least a second of the plurality of virtual applications from using the shared data.

Figure 5:
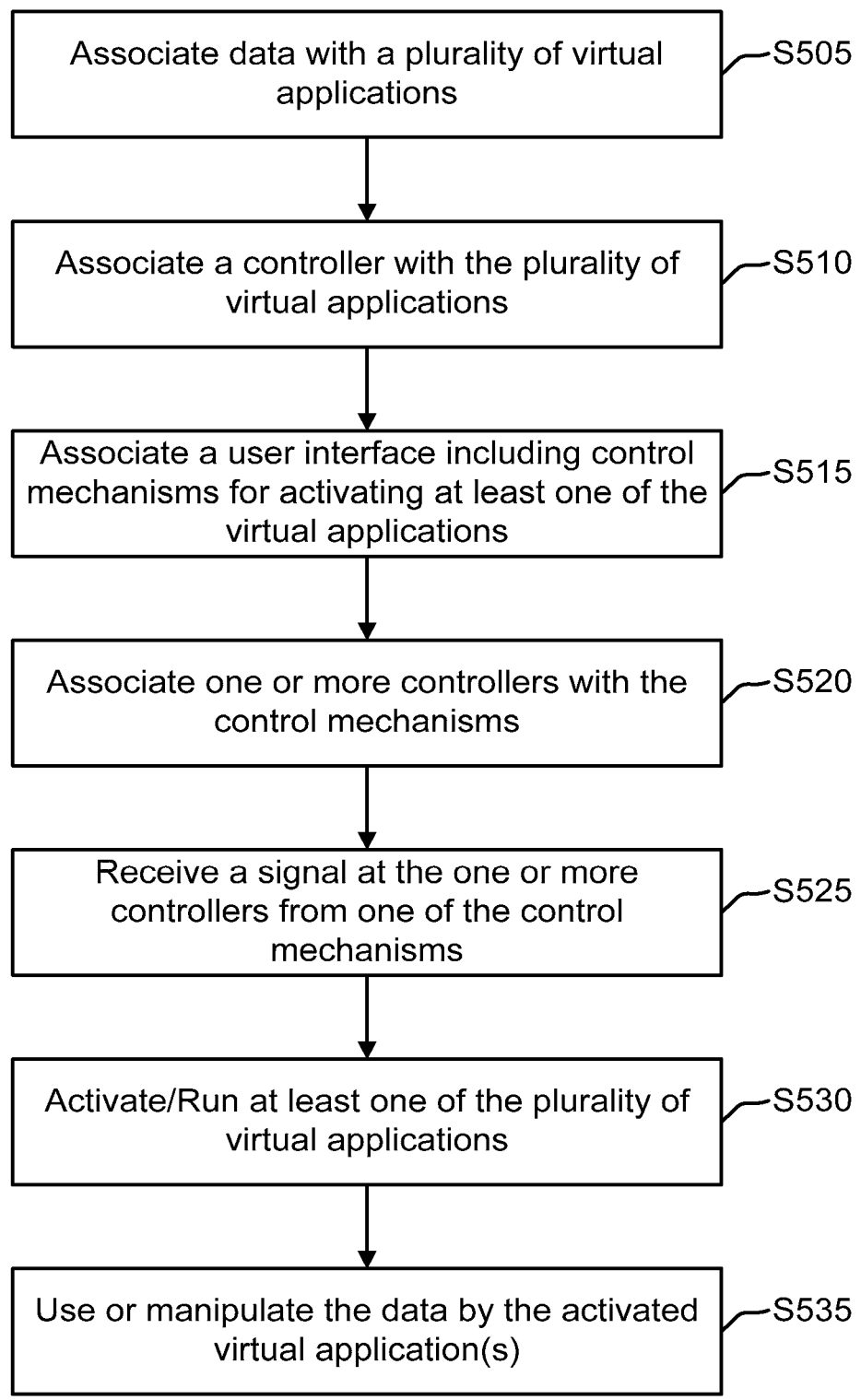
FIG. 5 illustrates a method for using large data sets in a virtual application according to at least one example embodiment.

FIG. 5 illustrates a method for using large data sets in a virtual application according to an example embodiment of the present application. Each of the steps of FIG. 5 may be performed by a client-server system (e.g., client-server system 300). Alternatively, each of the steps of FIG. 5 may be performed wholly by a client (e.g., client 305). Each of the steps of FIG. 5 may be performed by a processor associated with the client-server system and/or the client.

Referring to FIG. 5, in step S505 a processor, associated with one of a standalone machine, a client and/or a server (e.g., client 305 or server 310), associates shared data (e.g., data 240) with a plurality of virtual applications (e.g., VAP 210-1, 210-2 and 210-3). For example, the processor may instantiate an instance of a Co-MP 225. The Co-MP 225 associates data 240 with virtual applications VAP 210-1, 210-2 and 210-3 via VAC 235 and using Co-MP config 230.

In step S510, the processor associates a controller with the plurality of virtual applications. For example, VAC 235 may be associated with virtual applications VAP 210-1, 210-2 and 210-3. The association may be in a standalone machine, a client and/or a server (e.g., client 305 or server 310). For example, VAC 235 in client 305 may be associated with VAP 210-1, 210-2 and 210-3 in client 305 and VAC 235 in server 310 may be associated with VAP 210-1, 210-2 and 210-3 in server 310.

In step S515, the processor associates a user interface including control mechanisms for activating at least one of the plurality of virtual applications. For example, user interface 405 including application modules 410, 415, 420 may be associated with the virtual applications VAP 210-1, 210-2 and 210-3. As discussed above, this association may include associating a corresponding VAP Config 215-1, 215-2, 215-3 with an application module (e.g., 410, 415, 420).

In step S520, the processor associates one or more controllers with the control mechanisms. For example, controller 425 and/or run-time engine 430 may be associated with the user interface 405 including the application modules 410, 415, 420.

In step S525, the one or more controllers receive a signal from one of the control mechanisms. For example, if the user switches from application module 410 (View/Edit 2D Image) to application module 415 (View/Edit 3D Image), a control mechanism in at least one of application module 410 and/or application module 415 may trigger an event indicating the switch. The event or trigger may be transmitted to the controller 425 in the form of a message.

In step S530, the processor activates and/or runs at least one of the plurality of virtual applications. For example, the controller 425 reads and interprets the event message triggering the switch and communicates an instruction to the VAC 235. The VAC 235 will then de-activate VAP 210-1

(associated with View/Edit 2D Image through VAP Config 215-1) and activate VAP 210-2 (associated with View/Edit 3D Image through VAP Config 215-2). The shared data 240 may be associated with the activated (selected) one of the virtual applications. The VAC may re-configure Co-CP 220 with pluggable extension code (e.g., VAP 210-2) and configuration (e.g., VAP Config 215-2), the selected application may be displayed the screen with correct layout with minimal delay.

Further, if the user switches between virtual applications (e.g., VAP 210-1, 210-2 and 210-3) without closing them, the Co-CP 220 may reuse instances of virtual applications over and over to restore a former state for the user. For example, as discussed above, the controller 425 reads and interprets the event message triggering the switch and communicates an instruction to the VAC 235. The VAC 235 will then de-activate VAP 210-1 (associated with View/Edit 2D Image through VAP Config 215-1) and activate VAP 210-2 (associated with View/Edit 3D Image through VAP Config 215-2). However, activating and de-activating virtual applications may include restoring a previous state for the user (in addition to allowing the virtual application access to the shared data) and storing a current state of the user (in addition to excluding the virtual application from the shared data) by the Co-CP 220.

In step S535, the processor uses and/or manipulates the shared data by the activated virtual application(s). For example, the user may view or edit (and the like) a 3D Image that is displayed on a display device (e.g., a computer monitor associated with the user interface 405) following the activation of application module 415 and VAP 210-2.

Figure 6:
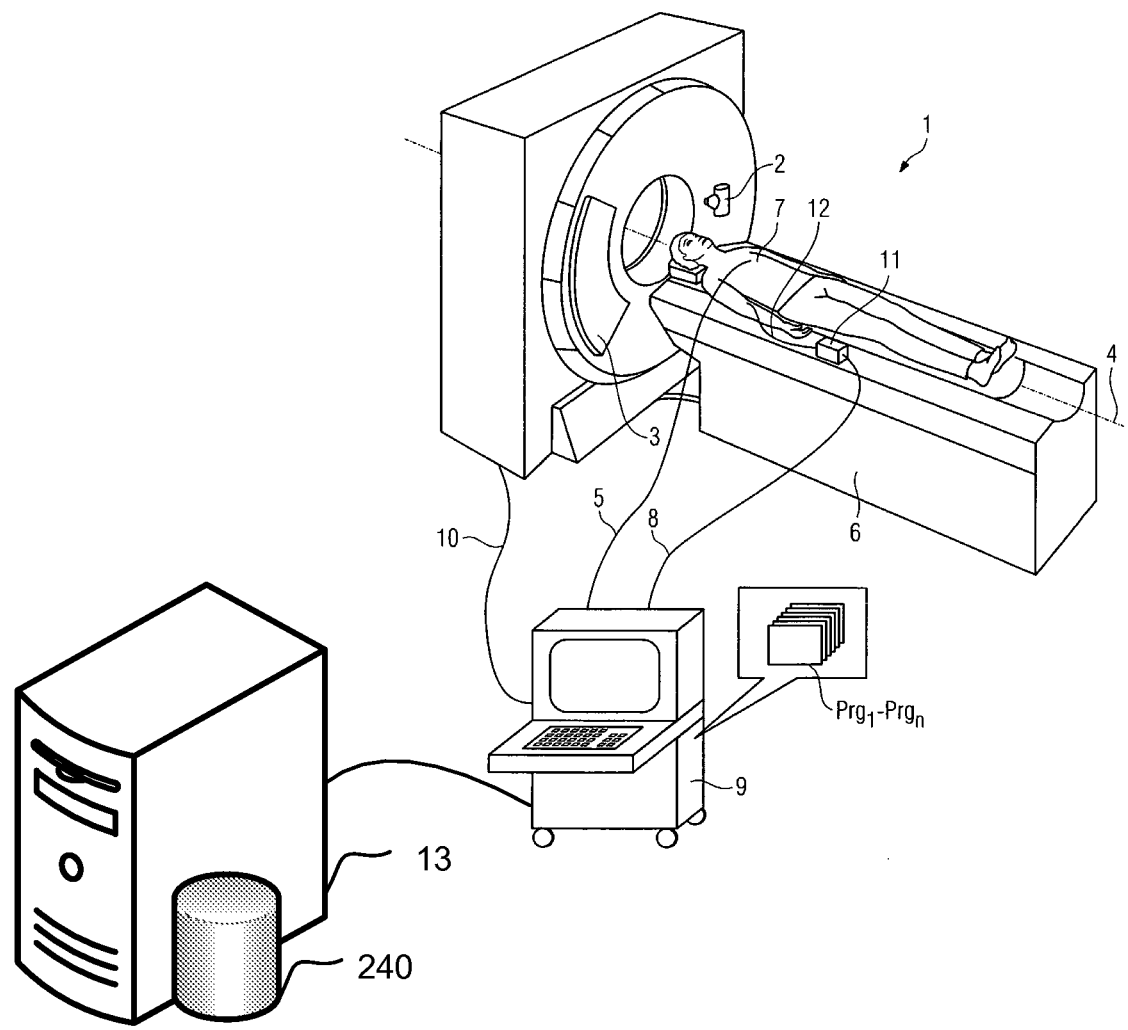
FIG. 6 illustrates a system for computed tomography according to example embodiments.

FIG. 6 illustrates an example embodiment of a system for computed tomography. The system for computed tomography 1 may be a medical work flow management system, for example. As shown in FIG. 6, the system for computed tomography 1 may include an X-ray tube 2, a detector 3, a system axis 4, an ECG lead 5, a displaceable patient couch 6, a patient 7, a control line for the injector 8, a control and arithmetic logic unit 9, a control and data line to the CT 10, an injector 11 an a contrast medium line 12.

As is illustrated by FIG. 6, the computed tomography system 1 may include the control and arithmetic logic unit 9 including data memories with programs $Prg_1$-$Prg_n$. As one skilled in the art will appreciate, individual method steps and control tasks may be distributed among different computers within the scope of the example embodiments. The control and arithmetic logic unit 9 shown here is connected via a control and data line 10 to the actual CT, which has an X-ray tube 2 and, oppositely thereto, a detector that is fastened on a gantry and can move on a circular track in order to scan the patient.

During a scanning operation, a patient 7 who is located on a couch 6 that can be displaced in the direction of the system axis 4, may be displaced in the direction of the system axis 4 such that, in the final analysis, spiral scanning takes place relative to the patient's coordinate system. The computed tomography system 1 additionally may include an ECG that is integrated in the arithmetic logic unit 9 and scans the heart rate of the patient 7 via the ECG line 5. Furthermore, the control and arithmetic logic unit 9 may use the control line 8 to operate an injector 11 with the aid of an integrated contrast medium pump, and via the hose line 12 depicted this injector 11 may inject the required contrast medium into the patient's 7 blood circulation at a prescribed flow rate.

According to an example embodiment, the programs $Prg_1$ to $Prg_n$ stored in the arithmetic logic and control unit may firstly push the patient 7 so far into the beam path of the CT that a so-called prescan of a cardiac artery can be carried out. There is no feeding of the patient 7 in the case of this prescan, rather, a tomogram of the heart may be produced only in a plane of low dose rate in order to establish the contrast medium filling of an artery essential to the examination.

If the patient 7 is located in the correct prescan position, the injector 11 may inject contrast medium at a prescribed flow rate, and either the operator may use the reconstructed tomogram output on a illustration screen to establish when there is a sufficient contrast medium filling in the observed cardiac artery, or an appropriate program can establish via automatic image processing whether sufficient contrast is present in the reconstructed image for a good illustration of the arteries.

As one skilled in the art will appreciate, each of the components of the computed tomography system 1 may be associated with a virtual application (e.g., VAP 210-1, 210-2 and 210-3). For example, X-ray tube 2 and detector 3 may have an associated virtual application associated with their functionality. Further, as one skilled in the art will appreciate, computed tomography image data may involve a large amount of data. The image data may be stored in a memory associated with the control and arithmetic logic unit 9. The image data may be stored in database server 13 as data 240.

The control and arithmetic logic unit 9 may include the client 305 and the database server 13 may include server 310. For example, in addition to applications for controlling the components of the computed tomography system 1, together in a client-server relationship (as described above with regard to FIG. 3, for example) the control and arithmetic logic unit 9 and the database server 13 may include at least one virtual application (e.g., VAP 210-1, 210-2 and 210-3) for accessing and/or manipulating image data acquired using the computed tomography system 1 and stored on the database server 13.

Although the above example was described with regard to a computed tomography system, example embodiments are not limited thereto. For example, a system of an example embodiment of the present application may be another type of imaging system (e.g., MRI, PET, etc.). Further, example embodiments are not limited to scanning (acquisition) steps of the clinical workflow. For example, example embodiments may be related to post processing, reading, and reporting workflow steps. Further, example embodiments are not limited to imaging systems. For example, example embodiments may be related to a clinical study system or other health care management system. Further, the control and arithmetic logic unit 9 may be a standalone computer accessing and/or manipulating data stored on the database server 13. The database server 13 may be an element of a medical data storage server, a business logic server, a hospital management systems server and the like.

In addition to the above example embodiments, the following capabilities offer additional flexibility when using the virtual applications architectures discussed above. The client-server distribution of all of the above elements may allow configurable and flexible deployments. The user interface on, for example client 305, may be optional. Some external mechanism, for example, a job handler, may start virtual application servers or back-ends only that may benefit from the identical advantages of the solution, and at the same time, synchronized via the VAC 235 on the client 305 and server 310, the user interface visualization may show the current progress.

The different virtual applications may be distributed over different processes or hardware (e.g., clients and servers), due to the distribution capability of the VAC 235. Further, there may be more than one client 305 and/or server 310. The virtual applications may be converted into regular physical applications by changing the configuration only, if the pluggable extension code (e.g., VAP 210-1, 210-2 and 210-3) and configuration (e.g., VAP Config 215-1, 215-2, 215-3) is re-used in dedicated instances of Co-MP 225 and Co-CP 220 with VAC 235 deactivated in the Co-MP config 230.

The virtual applications may be structured independently of each other. The virtual applications may be licensed and configured independently. The virtual applications may be added or removed form the application set flexibly at run-time, for example, depending on the data to be loaded (configurable Co-MP 225 policy), or decided statically at development time. Depending on the clinical process, a subset or all of the configured virtual applications may be chained in a way that closing the current application opens the next in the chain automatically, jumping over non-chained applications. Also in this scenario, the user may select applications randomly at the same time, no matter if the selected application was chained or non-chained.

Alternative embodiments of the invention may be implemented as a computer program product for use with a computer system, the processor program product being, for example, a series of processor instructions, code segments or program segments stored on a tangible or non-transitory data recording medium (processor readable medium), such as a diskette, CD-ROM, ROM, or fixed disk, or embodied in a computer data signal, the signal being transmitted over a tangible medium or a wireless medium, for example, microwave or infrared. The series of processor instructions, code segments or program segments can constitute all or part of the functionality of the methods of example embodiments described above, and may also be stored in any memory device, volatile or non-volatile, such as semiconductor, magnetic, optical or other memory device.

One embodiment of the present application includes a computer readable medium. The computer readable medium includes code segments that, when executed by a processor, cause the processor to associate a plurality of virtual applications with a shared data and associate a controller with the plurality of virtual applications such that the controller enables a first one or more virtual applications of the plurality of virtual applications to use the shared data and the controller excludes a second one or more virtual applications of the plurality of virtual applications from using the shared data.

Although the above example was described with regard to a computed tomography system, example embodiments are not limited thereto. For example, system may be another imaging system (e.g., MRI, PET, etc.). Further, example embodiments are not limited to imaging systems. For example, example embodiments may be related to a clinical study system or other health care management system. Further, as one skilled in the art will appreciate, example embodiments may be related to any system using large data such as aerial imagery or satellite images, but are not limited thereto.

While example embodiments have been particularly shown and described, it will be understood by one of ordinary skill in the art that variations in form and detail may be made therein without departing from the spirit and scope of the claims. The invention being thus described, it will be obvious that the same may be varied in many ways. Such variations are not to be regarded as a departure from the invention, and all such modifications are intended to be included within the scope of the invention.

We claim:
1. An apparatus, comprising:
a processor including
a control module including one or more first interfaces communicatively coupled to a data storage device, and one or more second interfaces communicatively coupled to a user interface, the control module being configured to retrieve data from the data storage device and share the data across a plurality of virtual applications of a single device, such that the plurality of virtual applications use a single instance of the shared data; and
an application controller communicatively coupled to the control module, the application controller being configured to select one or more of the plurality of virtual applications based on information received via at least one of the one or more second interfaces,
wherein the control module is configured to
receive the information from the user interface, the information including a selection of one or more virtual applications displayed on the user interface,
send a first message to the application controller based on the received information,
receive a second message from the application controller, the second message including an activation notification and a deactivation notification,
based on the activation notification, preload and associate the shared data with the selected one or more virtual applications by hosting ports for the selected one or more virtual applications to the shared data, and
based on the deactivation notification, save the shared data and disassociate a de-selected one or more other virtual applications from the shared data by removing ports for the de-selected one or more other virtual applications to the shared data; and
wherein, in response to receiving the first message, the application controller is configured to
determine, based on the first message, the one or more virtual applications to be selected and activated and the one or more other virtual applications to be de-selected and deactivated,
activate the determined one or more virtual applications,
deactivate the determined one or more other virtual applications,
send the second message to the control module, the second message indicating the activated one or more virtual applications and the de-activated one or more other virtual applications,
re-configure the activated one or more virtual applications with a pluggable extension code associated with a configuration file to configure a display format of the shared data, and
send a third message to each of the determined one or more virtual applications to configure the shared data.

2. The apparatus of claim 1, wherein the processor further comprises:
a hosting module, communicatively coupled to the control module and each of the plurality of virtual applications, the hosting module being configured to de-couple the plurality of virtual applications from at least one of the processor and an operating system associated with the apparatus.

3. The apparatus of claim 2, wherein the hosting module is further configured to:
provide one or more mechanisms for at least one of editing, merge-back and providing an availability of editing of the shared data, and
reuse instances of the plurality of virtual applications if the processor receives an instruction to switch between the plurality of virtual applications without closing the plurality of virtual applications.

4. The apparatus of claim 1, wherein the control module is further configured to associate the shared data by enabling the one or more virtual applications to modify the shared data.

5. The apparatus of claim 1, further comprising:
a memory configured to store a plurality of configuration files, the plurality of configuration files being associated with the control module and including information about virtual applications accessible using the user interface; wherein
the plurality of configuration files include the configuration file associated with the pluggable extension code.

6. The apparatus of claim 5, wherein the plurality of configuration files are dedicated files in a directory tree and include at least one of application name, position in a control area on the user interface and a link to a virtual application configuration file for each of the virtual applications accessible using the user interface.

7. The apparatus of claim 1, further comprising:
a memory configured to store a plurality of configuration files, each of the plurality of configuration files being associated with one of the plurality of virtual applications, such that one of the plurality of configuration files is processed when an associated virtual application is selected by the application controller; wherein
the plurality of configuration files include the configuration file associated with the pluggable extension code.

8. The apparatus of claim 1, wherein each of the one or more second interfaces includes one or more user triggers for selecting one or more of the plurality of virtual applications.

9. A system, comprising:
a plurality of apparatuses, each of the plurality of apparatuses including at least one processor, and the plurality of apparatuses including
a plurality of control modules, at least a first of the plurality of control modules including one or more first interfaces communicatively coupled to a data storage device and one or more second interfaces communicatively coupled to a user interface, the first control module being configured to retrieve data from the data storage device and share the data across a plurality of virtual applications such that the plurality of virtual applications use a single instance of the shared data, and
a plurality of application controllers, at least a first of the plurality of application controllers being communicatively coupled to the first control module and configured to select one or more of the plurality of virtual applications based on information received via at least one of the one or more second interfaces;
a third interface configured to communicatively couple the plurality of control modules associated with the plurality of apparatuses;
a fourth interface configured to communicatively couple the plurality of application controllers associated with the plurality of apparatuses; and
a plurality of fifth interfaces, each of the plurality of fifth interfaces configured to communicatively couple two or more of the plurality of virtual applications associated with the plurality of apparatuses, each of the two or more virtual applications being associated with a different one of the plurality of apparatuses;
wherein at least the first of the plurality of control modules is configured to
receive the information from the user interface, the information including a selection of one or more virtual applications displayed on the user interface, and a de-selection of one or more other virtual applications,
send, based on the received information, a first message to the first application controller,
receive a second message from the first application controller, the second message including an activation notification and a deactivation notification,
based on the activation notification, preload and associate the shared data with the selected one or more virtual applications by hosting ports for the selected one or more virtual applications to the shared data, and
based on the deactivation notification, save the shared data and disassociate the de-selected one or more other virtual applications from the shared data by removing ports for the de-selected one or more other virtual applications to the shared data; and
wherein, in response to receiving the first message, the first application controller is configured to
determine, based on the first message, the one or more virtual applications to be selected and activated and the one or more other virtual applications to be de-selected and deactivated,
activate the determined one or more virtual applications,
deactivate the determined one or more other virtual applications,
send the second message to the first control module, the second message indicating the activated one or more virtual applications and the de-activated one or more other virtual applications,
re-configure the activated one or more virtual applications with a pluggable extension code associated with a configuration file to configure a display format of the shared data,
and
send a third message to each of the determined one or more virtual applications to configure the shared data.

10. The system according to claim 9, wherein a first of the plurality of apparatuses is a client and a second of the plurality of apparatuses is a server.

11. The system according to claim 10, wherein
the client includes a memory to store a plurality of configuration files, the plurality of configuration files being associated with the first control module and including information about virtual applications accessible using the user interface; and
the plurality of configuration files include the configuration file associated with the pluggable extension code.

12. The system according to claim 11, wherein
the plurality of configuration files include dedicated files in a directory tree and include at least one of application name, position in the control area on the user interface and a link to a virtual application configuration file for each of the virtual applications accessible using the user interface; and
the plurality of configuration files include the configuration file associated with the pluggable extension code.

13. The system according to claim 10, wherein
the client includes a memory to store a plurality of configuration files, each of the plurality of configuration files being associated with one of the plurality of virtual applications, such that one of the plurality of configuration files is processed when an associated virtual application is selected by the first application controller; and
the plurality of configuration files include the configuration file associated with the pluggable extension code.

14. The system according to claim 10, wherein the server processes the shared data.

15. The system according to claim 10, wherein the client processes the shared data.

16. The system according to claim 10, wherein the client is a medical imaging device and the server is a medical data storage server.

17. The system according to claim 10, wherein a third of the plurality of apparatuses is a business logic server.

18. A method, comprising:
receiving, by a control module, information from a user interface, the information including a selection of one or more virtual applications and a de-selection of one or more other virtual applications displayed on the user interface, the control module being configured to retrieve data from a data storage device and share data across a plurality of virtual applications, the plurality of virtual applications belonging to a single device and configured to use a single instance of the shared data;
sending, by the control module, a first message to an application controller;
receiving, by the application controller, the first message from the control module;
determining, by the application controller based on the first message, the selected one or more virtual applications to be activated and the one or more other virtual applications to be de-selected and deactivated;
activating, by the application controller, the determined one or more virtual applications;
deactivating, by the application controller, the determined one or more other virtual applications;
re-configuring, by the application controller, the activated one or more virtual applications with a pluggable extension code associated with a configuration file to configure a display format of the shared data;
sending, by the application controller, a second message to the control module, the second message including an activation notification and a deactivation notification;
receiving, by the control module, the second message from the application controller;
based on the activation notification, preloading and associating, by the control module, the shared data with the selected one or more virtual applications by hosting ports for the selected one or more virtual applications to the shared data;
based on the deactivation notification, saving, by the control module, the shared data,
based on the deactivation notification, disassociating, by the control module, the de-selected one or more other virtual applications from the shared data by removing ports for the de-selected one or more other virtual applications to the shared data; and
sending, by the application controller, a third message to each of the determined one or more virtual applications to configure the shared data.

19. A non-transitory computer readable medium including code segments that, when executed by a processor, cause the processor to perform the method of claim 18.

20. A medical imaging device comprising the non-transitory computer readable medium of claim 19.

* * * * *